United States Patent
Liu et al.

(10) Patent No.: US 11,517,518 B2
(45) Date of Patent: Dec. 6, 2022

(54) TWO-STEP LONG-WEAR COSMETIC SYSTEM

(71) Applicant: L'ORÉAL, Paris (FR)

(72) Inventors: Tianyi Liu, Springfield, PA (US); Prasad S. Ranadive, Middlesex, NJ (US)

(73) Assignee: L'ORÉAL, Paris (FR)

( * ) Notice: Subject to any disclaimer, the term of this patent is extended or adjusted under 35 U.S.C. 154(b) by 0 days.

(21) Appl. No.: 16/522,069

(22) Filed: Jul. 25, 2019

(65) Prior Publication Data

US 2021/0022987 A1   Jan. 28, 2021

(51) Int. Cl.
| | | |
|---|---|---|
| *A61K 8/90* | (2006.01) | |
| *A61Q 1/04* | (2006.01) | |
| *A61K 8/891* | (2006.01) | |
| *A61K 8/92* | (2006.01) | |

(52) U.S. Cl.
CPC ............... *A61K 8/90* (2013.01); *A61K 8/891* (2013.01); *A61K 8/92* (2013.01); *A61Q 1/04* (2013.01)

(58) Field of Classification Search
None
See application file for complete search history.

(56) References Cited

U.S. PATENT DOCUMENTS

| | | | |
|---|---|---|---|
| 4,693,935 A | 9/1987 | Mazurek | |
| 4,972,037 A | 11/1990 | Garbe et al. | |
| 4,981,902 A | 1/1991 | Mitra et al. | |
| 4,981,903 A | 1/1991 | Garbe et al. | |
| 5,061,481 A | 10/1991 | Suzuki et al. | |
| 5,209,924 A | 5/1993 | Garbe et al. | |
| 5,219,560 A | 6/1993 | Suzuki et al. | |
| 5,262,087 A | 11/1993 | Tachibana et al. | |
| 5,468,477 A | 11/1995 | Kumar et al. | |
| 5,849,275 A | 12/1998 | Calello et al. | |
| 6,033,650 A | 3/2000 | Calello et al. | |
| 8,664,329 B2 * | 3/2014 | Liu ..................... | C09D 183/04 524/588 |
| 2007/0020205 A1 * | 1/2007 | Blin ........................ | A61Q 1/04 424/61 |
| 2007/0025940 A1 * | 2/2007 | Robert ................. | A61Q 19/001 424/64 |
| 2012/0301415 A1 | 11/2012 | Bui et al. | |

* cited by examiner

*Primary Examiner* — Tigabu Kassa
(74) *Attorney, Agent, or Firm* — Meagher Emanuel Laks Goldberg & Liao, LLP

(57) ABSTRACT

Disclosed is a transfer-resistant and long-lasting two-step cosmetic system, and a method for applying the cosmetic system. The disclosed system includes a first composition that includes a styrenic block copolymer, a silicone acrylate copolymer, and a volatile oil and a second composition that includes a silicone oil.

12 Claims, No Drawings

TWO-STEP LONG-WEAR COSMETIC SYSTEM

FIELD OF THE INVENTION

The present invention relates to two-step lip compositions having a top coat composition that provide one or more benefits such as transfer-resistance and long-lasting finish.

BACKGROUND

Commercially available long wear cosmetics are typically comprised of a silicone resin, such as MQ resin, and a plasticizing agent. However, these products tend to have tacky feel. The feel of these products can be improved by incorporating silicone polymers, and shine can be improved by incorporating non-volatile solvents. However, these additional ingredients reduce the wear properties of the underlying formulation. As such, a long wear cosmetic composition having acceptable aesthetics is desirable.

BRIEF SUMMARY

A first aspect of the present disclosure is a two-step, long-wear cosmetic system, involving two compositions: (1) a first composition that utilizes a styrenic block copolymer, a silicone acrylate copolymer, and a volatile oil; and (2) a second composition that utilizes a silicone oil.

The first composition may also include a colorant, possibly at an amount of between 0.001 and 5% by weight. The styrenic block copolymer may be a di- or tri-block copolymer comprised of at least one block of a styrene monomer and at least one block of at least one other monomer chosen from ethylene, butylene, and butadiene, and/or may be present in an amount between 1 and 30% by weight. The silicone acrylate copolymer may contain a polydimethylsiloxane graft and/or may be present in an amount from between 10 and 95% by weight. The volatile oil may be a branched alkane having between 10 and 20 carbons, and/or may be present in an amount between 10 and 90% by weight.

The second composition may also include a phenylated silicone and/or a silicone wax such as stearyl-dimethicone wax. The silicone oil in the second composition may be a polydimethylsiloxane, and/or have a viscosity between 100 cst and 1,000,000 cst, and/or be present in an amount between 30 and 100% by weight.

A second aspect of the present disclosure is a method for applying a long-wear cosmetic system. The method consists of applying to lips two compositions, the first composition applied before the second. The first composition should comprise between 1 and 30% by weight of a styrenic block copolymer, between 10 and 95% by weight of a silicone acrylate copolymer, and between 10 and 90% by weight a volatile oil. The second composition should comprise between 30 and 100% by weight of a silicone oil. The first composition may include a colorant. The second composition may also include a phenylated silicone and/or a stearyl-dimethicone wax. The silicone oil in the second composition may be a polydimethylsiloxane, and/or have a viscosity between 100 cst and 1,000,000 cst, and/or be present in an amount between 30 and 100% by weight.

A third aspect of the present disclosure is a long-wear lip product prepared by a process that includes applying a first composition to lips, then applying a second composition to the lips, where the first composition contains between 1 and 30% by weight of a styrenic block copolymer and between 10 and 95% by weight of a silicone acrylate copolymer, while the second composition contains between 30 and 100% by weight of a silicone oil.

DETAILED DESCRIPTION

As used herein, articles such as "a" and "an" when used in a claim, are understood to mean one or more of what is claimed or described.

As used herein, the term "about [a number]" is intended to include values rounded to the appropriate significant digit. Thus, "about 1" would be intended to include values between 0.5 and 1.5, whereas "about 1.0" would be intended to include values between 0.95 and 1.05.

As used herein, the term "at least one" means one or more and thus includes individual components as well as mixtures/combinations.

As used herein, the terms "include", "includes" and "including" are meant to be non-limiting.

As used herein, the term "oil" means a fatty substance that is liquid at room temperature (25° C.).

As used herein, the term "silicone oil" means a polyorganosiloxane comprising alkylsiloxane repeating units.

As used herein, the term "volatile oil" denotes an oil (or non-aqueous medium) liable to evaporate on skin contact in less than one hour, at ambient temperature and atmospheric pressure.

A first aspect of the present disclosure is a long-lasting, two-step cosmetic system. The system includes a first composition that comprises (a) a styrenic block copolymer, (b) a silicone acrylate copolymer, and (c) a volatile oil. The first composition may also include other components, such as a colorant. Additionally, the first composition may have a structural recovery rate in the range of about 10 seconds to about 50 seconds. In some embodiments, the structural recovery rate is in the range of about 10 seconds to about 30 seconds.

The second composition may comprise, consist essentially of, or consist of, a silicone oil. The second composition may also include other components, such as a phenylated silicone and/or a silicone wax such as stearyl-dimethicone wax.

In some embodiments, the system may be provided as a kit, with the first composition is provided in a first container and the second composition is provided in a second container that is co-packaged with the first container. In some embodiments, the kit may include instructions for use.

Styrenic Block Copolymer

The first composition in the cosmetic system should include at least one styrenic block copolymer.

Suitable examples of styrenic block copolymers include the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylene/propylene-styrene, or styrene-ethylene/butylene-styrene.

The Kraton™ di-block is preferably the AB block type such as styrene-ethylene/propylene, styrene-ethylene/butylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (triblock), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

Particularly useful is hydrogenated styrene/butadiene copolymer (Kraton G1657), commercially available from Kraton Polymers.

Preferably, the at least one styrenic block copolymer is present in an amount ranging from about 1 percent to about 30 percent by weight of active material with respect to the total weight of the first composition. In some embodiments, the at least one styrenic block copolymer is present in an amount ranging from about 1 percent to about 15 percent, from about 1 percent to about 10 percent, from about 1 percent to about 5 percent, from about 5 percent to about 10 percent, or from about 10 percent to about 15 percent by weight of active material.

Silicone Acrylate Copolymer

The first composition in the cosmetic system should include at least one silicone acrylate copolymer.

Suitable examples of silicone acrylate copolymers include silicone/(meth)acrylate copolymers, such as those described in U.S. Pat. Nos. 5,061,481, 5,219,560, 5,262,087 and US 2012/0301415, the entire contents of all of which are hereby incorporated by reference.

Suitable examples also include polymers derived from non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the products sold under the tradenames KP-545 (cyclopentasiloxane (and) acrylates/dimethicone copolymer), KP-543 (butyl acetate (and) acrylates/dimethicone copolymer), KP-549 (methyl trimethicone (and) acrylates/dimethicone copolymer), KP-550 (tentative INCI name: isododecane (and) acrylate/dimethicone copolymer), and mixtures thereof. Additional examples include the acrylate/dimethicone copolymers sold by Dow Corning under the tradenames FA 4001 CM SILICONE ACRYLATE (cyclopentasiloxane (and) acrylates/polytrimethylsiloxymethacrylate copolymer) and FA 4002 ID SILICONE ACRYLATE (isododecane (and) acrylates/polytrimethylsiloxymethacrylate Copolymer), and mixtures thereof.

Suitable examples also include polymers comprising a backbone chosen from vinyl polymers, methacrylic polymers, and acrylic polymers, and at least one chain chosen from pendant siloxane groups. Non-limiting examples of such polymers and their synthesis are disclosed, for example, in U.S. Pat. Nos. 4,972,037, 5,061,481, 5,209,924, 5,849,275, and 6,033,650, the entire contents of all of which are hereby incorporated by reference. These polymers may be sourced from various companies. One such company is 3M Company, which offers these types of polymers under the tradenames "Silicone Plus" polymers (for example, poly(isobutyl methacrylate-co-methyl FOSEA)-g-poly(dimethylsiloxane), sold under the tradename SA 70-5 IBMMF).

Suitable examples also include silicone/acrylate graft terpolymers. Suitable examples also include polymers comprises a backbone chosen from vinyl backbones, methacrylic backbones, and acrylic polymeric backbones and further comprises at least one pendant siloxane group. Non-limiting examples of such polymers are disclosed in U.S. Pat. Nos. 4,693,935, 4,981,903, and 4,981,902, the entire contents of all of which are hereby incorporated by reference.

Suitable examples also include those described in U.S. Pat. No. 5,468,477, the entire contents of all of which are hereby incorporated by reference. A non-limiting example of these polymers is poly(dimethylsiloxane)-g-poly(isobutyl methacrylate), which is commercially available from 3M Company under the tradename VS 70 IBM.

In some embodiments, suitable silicone acrylate copolymers have a glass transition temperature ($T_g$) of greater than 20° C., in some embodiments greater than about 25° C.

The silicone acrylate copolymer should be present in the first composition in an amount ranging from about 10 percent to about 95 percent by weight.

Volatile Oil

The first composition in the cosmetic system should include at least one volatile oil.

The volatile oil may have an evaporation rate of between 0.01 and 200 mg/cm$^2$/mn, inclusive. To measure this evaporation rate, 15 g of oil or an oil mixture to be tested may be introduced into a crystallizer with a diameter of 7 cm, placed on a scale located in a large chamber of around 0.3 m$^3$, with controlled temperature, at 25° C., and hygrometry, at 50% relative humidity. The liquid is left to evaporate freely, without stirring, by allowing ventilation with a fan (e.g., PAPST-MOTOREN, reference 8550 N, rotating at 2700 rpm) arranged vertically above the crystallizer containing said oil or said mixture, with the blades being directed toward the crystallizer and at a distance of 20 cm with respect to the crystallizer base. The mass of oil remaining in the crystallizer is measured at regular intervals. The evaporation rates are expressed in mg of oil evaporated per unit of surface (cm$^2$) and per unit of time (minutes).

The volatile oil may be a hydrocarbon oil, which may be chosen from branched or unbranched hydrocarbon oils. Preferably, the hydrocarbon oil has from 7 to 20 carbon atoms, and more preferably from 10 to 20 carbon atoms. Preferably, the hydrocarbon oil comprises C8-C16 branched alkanes such as C8-C16 iso-alkanes (also called isoparaffins), isododecane, isodecane, isohexadecane. Such oils may be sold under the trade names of Isopars or Permethyls. The volatile oil may also be chosen from C8-C16 branched esters such as isohexyl neopentanoate.

The first composition may include two or more volatile oils. Preferably, the hydrocarbon volatile oil having from 10 to 20 carbon atoms is chosen from among isododecane, isodecane, isohexadecane and mixtures thereof, and is in particular isododecane and isohexadecane.

The volatile oil should be present in the first composition in an amount between 10 and 90% by weight.

Colorants

According to certain embodiments of the present application, the first composition may also utilize at least one colorant. In certain embodiments, the colorant is a pigment, a pearlescent agent, or a combination thereof. The combined colorants should be present in the first composition in a total amount of between 0.001 and 5% by weight in the first composition.

In preferred embodiments, the second composition contains no colorant.

Suitable colorants include, but are not limited to, lipophilic dyes, pigments and pearlescent agents, and their mixtures. Any colorant typically found in lipstick compositions can be used.

Suitable examples of fat-soluble dyes are, for example, Sudan red, DC Red 17, DC Green 6, β-carotene, soybean oil, Sudan brown, DC Yellow 11, DC Violet 2, DC Orange 5 and quinoline yellow.

Suitable pigments can be white or colored, inorganic and/or organic and coated or uncoated. Mention may be made, for example, of inorganic pigments such as titanium dioxide, optionally surface treated, zirconium or cerium oxides and iron or chromium oxides, manganese violet, ultramarine blue, chromium hydrate and ferric blue. Mention may also be made, among organic pigments, of carbon black, pigments of D & C type and lakes based on cochineal carmine or on barium, strontium, calcium or aluminum, such as D&C Red No. 10, 11, 12, and 13, D&C Red No. 7, D&C Red No. 5 and 6, and D&D Red No. 34, as well as lakes such as D&C Yellow Lake No. 5 and D&C Red Lake No. 2.

Suitable pearlescents may also be included, and may be chosen from, for example, white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride.

Color additives, such as natural extracts, may also be appropriate in various embodiments. One such example is spirulina paltensis extract, although other extracts may also be appropriate.

Silicone Oil

The second composition should include at least one silicone oil. The second composition may comprise, consist essentially of, or consist of the at least one silicone oil.

The alkyl groups in the alkylsiloxane repeat units preferably comprise from 1 to 6 carbon atoms and preferably being unsubstituted. In particular, the linear silicone oils are preferably chosen from polydimethylsiloxanes (INCI name: dimethicone), preferably of formula:

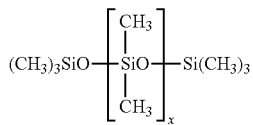

in which x is an integer chosen so as to have a fluid compound.

In preferred embodiments, the silicone oil has a viscosity of between about 100 cst and about 1,000,000 cst.

The silicone oil should be present in the second composition in an amount between 30 and 100% by weight. A silicone oil should not be present in the first composition.

While not intending to be bound by theory, it is hypothesized that the silicone oil of the present disclosure functions by inducing a physical curing of the first layer. The rate of curing through this physical interaction is faster than conventional chemical curing of the surface through reactive silicones (seconds comparing to tens of minutes), and significantly shortens the consumer waiting time. After curing, the composition also shows self-healing property. It is hypothesized that the physical curing of the styrenic block copolymer and silicone acrylate copolymer in the first composition can be influenced by the viscosity of the silicone oil. It is further hypothesized that the gelling interaction between blends of silicone acrylate copolymer and the silicone oil "seal" the first composition and provide for a non-transferring and non-sticky final composition.

To determine the impact of the silicone oil on the hypothesized curing, zero shear viscosity may be measured. In one example, several samples were prepared, each combining Shin-Etsu's KP-550 at a 60/40 ratio with a dimethicone. Each dimethicone had a viscosity between 6 cst and 1,000,000 cst. The blends were produced by combining the materials, then using high-speed mixing for 5 minutes at 2350 rpm. About 1 gram of each tested blend was deposited onto the rheometer platform. A 40 mm flat plate was used as a rheology probe with a gap of 1000 μm between the platform and the probe. Each sample was first equilibrated at 25° C. for 20 seconds, then a shear rate flow experiment was performed. The duration of each experiment was 10 minutes, having shear rate changes from 0.001-1000/s, with 5 data points recorded within each decade. After each experiment, a zero-shear viscosity was determined from a log (viscosity) vs. log(shear rate) plot, by linear fitting the initial plateau region to intersect with y-axis. This value represents the viscosity of each formula under unperturbed situation. Zero shear viscosity of each formula, measured at 25° C., is listed in Table 1, below. As can be seen, in this example, the zero-shear viscosity peaked at 1,000 cst, and dimethicones with viscosities in the range of 100 cst to 1,000,000 cst may induce changes in the curing and/or curing rate.

Table 1—Blend Viscosities

TABLE 1

| Blend Viscosities | |
| --- | --- |
| Blend Description | Viscosity (Pa s) |
| KP550 + 6 cst dimethicone | 0.45 |
| KP550 + 50 cst dimethicone | 0.363 |
| KP550 + 100 cst dimethicone | 39.95 |
| KP550 + 1 k cst dimethicone | 27000 |
| KP550 + 60 k cst dimethicone | 6324.56 |
| KP550 + 500 k cst dimethicone | 6973.8 |
| KP550 + 1 M cst dimethicone | 1448.92 |

Based on the information in Table 1, this hypothesis was further tested via two samples—Shin-Etsu's KP-550 is isododecane with a 1,000 cst dimethicone, and Kraton G1657 in isododecane with a 1,000 cst dimethicone. In this example, a rheometer was used to characterize the physical curing time. About 0.6 g of the first portion of each sample was placed on the platform, then about 0.4 g of the dimethicone was deposited on top of that. A 40 mm flat plate is used as a rheology probe with a gap of 1000 μm between the platform and the probe. Time-sweep is performed by using strain=0.1%, and angular frequency=1 rad/s. Curing time is determined as the time at which the storage modulus equals the loss modulus. In this example, the KP-550 sample had a curing time of 276.39 seconds, while the Kraton sample had a curing time of 11.70 seconds.

Broadly speaking, the system functions by first applying the first composition to e.g., lips, where the first composition comprises a styrenic block copolymer and silicone acrylate copolymer. Then the second composition, which comprises a silicone oil, is applied over the first composition, that theoretically induces a physical curing of the first layer, thereby forming a lip product with improved performance characteristics. In various embodiments, the composition of the two compositions should be chosen such that a 60/40 blend has a blend viscosity of at least 20 Pa s. at least 200 Pa s, at least 2,000 Pa s, or at least 20,000 Pa s, as tested according to the method described above.

Additional Components

The second composition may also include a phenylated silicone. This phenylated silicone may be a polyphenylmethylsiloxane or a phenyltrimethicone, or a mixture of various phenylated silicones. Examples of suitable phenylated silicones include DC556 and SF558 sold commercially by Dow Corning.

The second composition may also include a silicone wax. They may also be silicone waxes, referred to as alkyl, alkoxy or esters of poly(di)methylsiloxane silicones, which are polymers that comprise repeating dimethylsiloxy units in combination alkyl siloxy units wherein the long chain alkyl is generally a fatty chain that provides a wax-like character to the silicone. Such silicones include, but are not limited to stearoxydimethicone, behenoxy dimethicone, stearyl dimethicone, cetearyl dimethicone, and the like which are solid at 40° C. Preferably, when used, the silicone wax is stearyl dimethicone. Examples of suitable silicone waxes include those sold under the Abil brand by Evonik.

EXAMPLES

Referring to the compositions listed in Tables 2 and 3, the first three ingredients were combined, then heated to 95° C., mixed until homogenous, then cooled to room temperature. The colorants were then added slowly while mixing, forming the first composition. The pigment was first pre-dispersed in the silicone acrylate copolymer and a portion of the volatile oil using a homogenizer. The rest of the ingredients were then combined into the pigment dispersion by mixing at room temperature. The pearls were added slowly while mixing at room temperature to form the final first composition. All ingredients from the second composition were mixed at room temperature until homogenous. The first and second compositions were then each transferred into a desired container.

TABLE 2

Disclosed Formulations

| Material | Form. 1 % w/w | Form. 2 % w/w | Form. 3 % w/w |
|---|---|---|---|
| First Composition | | | |
| Styrenic Block Copolymer | 1-15% | 1-15% | 1-15% |
| Silicone Acrylate Copolymer | 60-90% | 60-90% | 60-90% |
| Volatile Oil | 1-20% | 1-20% | 1-20% |
| Colorant (Pearls) | — | 0.1-5% | — |
| Colorants (Pigments) | — | — | 0.1-5% |
| Second Composition | | | |
| Dimethicone | 100% | 100% | 100% |

TABLE 3

Comparative Formulations

| Material | Form. 4 % w/w | Form. 5 % w/w | Form. 6 % w/w |
|---|---|---|---|
| First Composition | | | |
| Styrenic Block Copolymer | — | 1-15% | 1-15% |
| Silicone Acrylate Copolymer | 60-90% | — | 60-90% |
| Volatile Oil | 1-20% | 1-20% | 1-20% |
| Colorant (Pearls) | — | — | — |
| Colorants (Pigments) | — | — | — |
| Second Composition | | | |
| Dimethicone | 100% | 100% | — |

Evaluations

The formulations were evaluated at 25° C. based on structural recovery rate, elasticity, critical strain, zero shear viscosity, and transfer. The results are summarized in Table 4.

TABLE 4

Summary of Evaluations

| Evaluation | Form. 1 | Form. 2 | Form. 3 | Form. 4 | Form. 5 | Form. 6 |
|---|---|---|---|---|---|---|
| Structural Recovery Rate (s) | 10.5 | 24.6 | 11.3 | <2 | <2 | 10.5 |
| Elasticity | 396.52 | 396.53 | 300.45 | 1874.33 | 168.65 | 25.11 |
| Critical Strain (%) | 10.15 | 10.15 | 8.24 | 27.52 | 26.45 | 25.25 |
| Zero Shear Viscosity (Pa · s) | 34.57 | 36.54 | 50.73 | 0.36 | 0.45 | 34.57 |
| Transfer (%) | 5.2 | 6.0 | 4.7 | 10.4 | 14.5 | 0 |

Structural Recovery Rate

To have the buildable property and thick-film formation ability, the structural recovery rate of the first composition should not be too fast nor too slow. Structural recovery rate also characterizes the self-healing property of the thick film. To measure structural recovery rate, about 1 gram of first composition is deposited on to a bottom plate. A 40 mm flat plate is used as a rheology probe with a gap of 1000 μm between the bottom plate and the probe. Each sample was equilibrated at 25° C. Sample was pre-sheared for 10 s at a shear rate of 30 sec$^{-1}$, then time sweep measurement is performed at 0.1% strain and 10 rad/s angular frequency for 300 s. The characteristic recovery time is calculated from fitting the equation below $$G'(t)=G'_0+(G'_\infty-G'_0)(1-e^{t/\tau})$$

Where G' is the shear storage modulus and the subscripts refer to frequency, τ is structural recovery rate of the composition.

As can be seen in Table 4, the disclosed compositions (Forms 1-3) have recovery rates between 10 sec and 30 sec, which is accepted as being neither too fast nor too slow for most applications. Formulas 4 and 5, for example, have recover rates of less than 2 seconds, which may be considered too fast for some applications.

Elasticity

To measure elasticity, the first and second compositions are first mixed at a 60:40 ratio. The elasticity of each combined composition is evaluated using a rheometer with a platform at 25° C., by measuring the storage modulus at an angular frequency=1 rad/s and an oscillating strain of 1%.

Critical Strain

To measure critical strain, the first and second compositions are first mixed at a 60:40 ratio. The elasticity of each combined composition is evaluated using a rheometer with a platform at 25° C., by measuring the storage modulus at an angular frequency=1 rad/s, using known rheological techniques.

Zero Shear Viscosity

To measure Zero Shear Viscosity, about 1 gram of each first composition was first deposited onto the platform of a rheometer. A 40 mm flat plate was used as a rheology probe with a gap of 1000 μm between the platform and the probe. Each sample was first equilibrated at 25° C. for 20 seconds, then a shear rate flow experiment was performed. The duration of each test was 10 minutes, with shear rate changing from 0.001-1000/s, with 5 data points recorded within each decade. After the experiment, a zero-shear viscosity is determined from a log(viscosity) vs. log(shear rate) plot, by linear fitting the initial plateau region to intersect with y-axis. This value represents the viscosity of each formula under unperturbed situation.

Transfer

To measure transfer, about a 10 mg quantity of the first composition was deposited onto a 2 cm×2 cm bio-skin square, and the actual mass was recorded. Immediately afterwards, about a 6 mg quantity of the second composition was deposited onto the first composition. The bio-skin square was then dried at room temperature for 10 minutes. Afterwards, a separate bio-skin square is pressed onto the coated one, and a 1 kg weight is applied. The mass transferred to the separate bio-skin square is measured, and the percent transferred is calculated by dividing the mass transferred by the original mass.

Those skilled in the art will recognize or be able to ascertain using no more than routine experimentation, many equivalents to the specific embodiments of the invention described herein. Such equivalents are intended to be encompassed by the following claims.

What is claimed is:

1. A two-step cosmetic system comprising:
   a first composition including
      1-15% by weight of a styrenic block copolymer;
      60-90% by weight of a silicone acrylate copolymer present in an amount between 60% and 90% by weight of the first composition; and
      1-20% of a volatile oil; and
   a second composition including a silicone oil,
      wherein the silicone oil has a viscosity between 100 cst and 1,000,000 cst, and
      wherein a critical strain of the system is less than 25%.

2. The two-step cosmetic system according to claim 1, wherein the first composition also includes a colorant.

3. The two-step cosmetic system according to claim 2, wherein the colorant is present in an amount between 0.001 and 5% by weight in the first composition.

4. The two-step cosmetic system according to claim 1, wherein the styrenic block copolymer is a di- or tri-block copolymer comprised of at least one block of a styrene monomer and at least one block of at least one other monomer selected from the group consisting of ethylene, butylene, and butadiene.

5. The two-step cosmetic system according to claim 1, wherein the silicone acrylate copolymer contains a polydimethylsiloxane graft.

6. The two-step cosmetic system according to claim 1, wherein the volatile oil is a branched alkane having between 10 and 20 carbons.

7. The two-step cosmetic system according to claim 1, wherein the silicone oil is a polydimethylsiloxane.

8. The two-step cosmetic system according to claim 1, wherein the second composition consists of the silicone oil.

9. A long-wear lip product prepared by a process comprising the steps of:
   applying a first composition to lips, the first composition including
      1-15% by weight of a styrenic block copolymer; and
      60-90% by weight of a silicone acrylate copolymer; and
      1-20% of a volatile oil; and
   applying a second composition to the lips, the second composition including between 30% and 100% by weight of a silicone oil,
      wherein the silicone oil has a viscosity between 100 cst and 1,000,000 cst, and
      wherein a critical strain of the system is less than 25%.

10. The two-step cosmetic system according to claim 1, wherein the second composition further comprises a phenylated silicone.

11. The two-step cosmetic system according to claim 1, wherein the second composition further comprises a stearyldimethicone wax.

12. The two-step cosmetic system according to claim 1, wherein the critical strain is ≤10.15%.

* * * * *